United States Patent
Ouchi

(10) Patent No.: US 6,193,666 B1
(45) Date of Patent: Feb. 27, 2001

(54) TIP OF ULTRASONIC ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/460,419

(22) Filed: Dec. 14, 1999

(30) Foreign Application Priority Data

Dec. 17, 1998  (JP) .................................................. 10-358657

(51) Int. Cl.[7] .................................................. A61B 8/00
(52) U.S. Cl. .......................................... 600/459; 600/463
(58) Field of Search .................................. 600/459, 460, 600/463, 461, 466, 464

(56) References Cited

U.S. PATENT DOCUMENTS

| | | | |
|---|---|---|---|
| 5,596,989 | * | 1/1997 | Morita .................................. 600/463 |
| 5,762,067 | * | 6/1998 | Dunham et al. ...................... 600/460 |
| 5,967,990 | * | 10/1999 | Thierman et al. .................... 600/459 |
| 5,976,073 | | 11/1999 | Ouchi . |
| 6,074,349 | * | 6/2000 | Crowley ................................ 600/463 |

FOREIGN PATENT DOCUMENTS

| | | |
|---|---|---|
| 2265533 | 10/1990 | (JP) . |
| 2265534 | 10/1990 | (JP) . |
| 2265535 | 10/1990 | (JP) . |
| 2271843 | 11/1990 | (JP) . |

* cited by examiner

*Primary Examiner*—Marvin M. Lateef
*Assistant Examiner*—Maulin Patel
(74) *Attorney, Agent, or Firm*—Greenblum & Bernstein, P.L.C.

(57) ABSTRACT

A tip of an ultrasonic endoscope has an instrument-inserting channel formed with an exit opening directed forward and opened at a distal end face of an insertion portion of the endoscope. An ultrasonic oscillator array for radial scan is provided annularly around the exit opening of the instrument-inserting channel. An optical viewing window for viewing obliquely forward is provided rearward of the ultrasonic oscillator array in such a way that its visual field covers both a distal end portion of an instrument projected from the instrument-inserting channel and a direction of ultrasonic scan with the ultrasonic oscillator array.

14 Claims, 3 Drawing Sheets

TIP OF ULTRASONIC ENDOSCOPE

BACKGROUND OF THE INVENTION

The present invention relates to the tip of an ultrasonic endoscope, which is to be inserted into a body cavity to perform ultrasonic scan and optical viewing simultaneously.

The tip of the insertion portion of an ultrasonic endoscope is equipped with an ultrasonic wave transmitting/receiving member and an optical viewing member. An instrument-inserting channel is also provided in the tip of the insertion portion of the ultrasonic endoscope so that an instrument such as one for injecting a liquid into the body can be passed through the instrument-inserting channel. Because of this structural complexity, the tip of the insertion portion of the ultrasonic endoscope is inevitably bulky and causes greater pain to the patient under examination than in the case of ordinary endoscopes.

An instrument projects from the tip of the insertion portion of an ultrasonic endoscope in various directions depending upon its design specifications. A forward projecting layout is recommended from the viewpoint of space economy, making the tip of the insertion portion the most compact in size.

A typical forward projecting layout is described in Unexamined Published Japanese Patent Application (kokai) No. 265535/1990, and it is characterized in that both the exit opening of the instrument-inserting channel and the viewing window are provided at the end face of the tip of the insertion portion of an ultrasonic endoscope and that an ultrasonic oscillator array for radial scan is provided annularly around the tip of the insertion portion.

However, if the viewing window is provided at the end face of the tip of the insertion portion and the ultrasonic oscillator array annularly around the tip of the insertion portion, the direction of ultrasonic scan is out of the visual field of optical viewing. Therefore, the site under ultrasonic scan cannot be viewed optically at the same time, making it impossible to perform reliable examination smoothly.

SUMMARY OF THE INVENTION

An object, therefore, of the invention is to provide the tip of an ultrasonic endoscope that is small enough to reduce the pain the patient has to endure and which yet allows the site under ultrasonic scan to be optically viewed at the same time, thus ensuring that reliable examination is performed smoothly.

To attain the above-noted object, the present invention provides a novel arrangement for the tip of an ultrasonic endoscope, wherein an optical viewing window for viewing forward at an angle is provided backward of an ultrasonic oscillator array. This arrangement makes it possible for an operator to optically view or visually observe the site being subjected to ultrasonic scan.

A tip of an ultrasonic endoscope according to a preferred embodiment includes: an instrument-inserting channel formed with an exit opening directed forward and opened at a distal end face of an insertion portion of the endoscope; an ultrasonic oscillator array for radial scan that is provided annularly around the exit opening of the instrument-inserting channel; and an optical viewing window for viewing obliquely forward that is provided rearward of the ultrasonic oscillator array in such a way that its visual field covers both a distal end portion of an instrument projected from the instrument-inserting channel and a direction of ultrasonic scan with the ultrasonic oscillator array.

If desired, the radial ultrasonic oscillator array may be provided coaxially with said instrument-inserting channel. Alternatively, the longitudinal axis of said annular ultrasonic oscillator array may be formed at an angle with that of said instrument-inserting channel in such a direction that the ultrasonic scan direction is away from said optical viewing window.

The present disclosure relates to the subject matter contained in Japanese patent application No. Hei. 10-358657 (filed on Dec. 17, 1998), which is expressly incorporated herein by reference in its entirety.

DESCRIPTION OF THE PREFERRED EMBODIMENT

Figure 1:
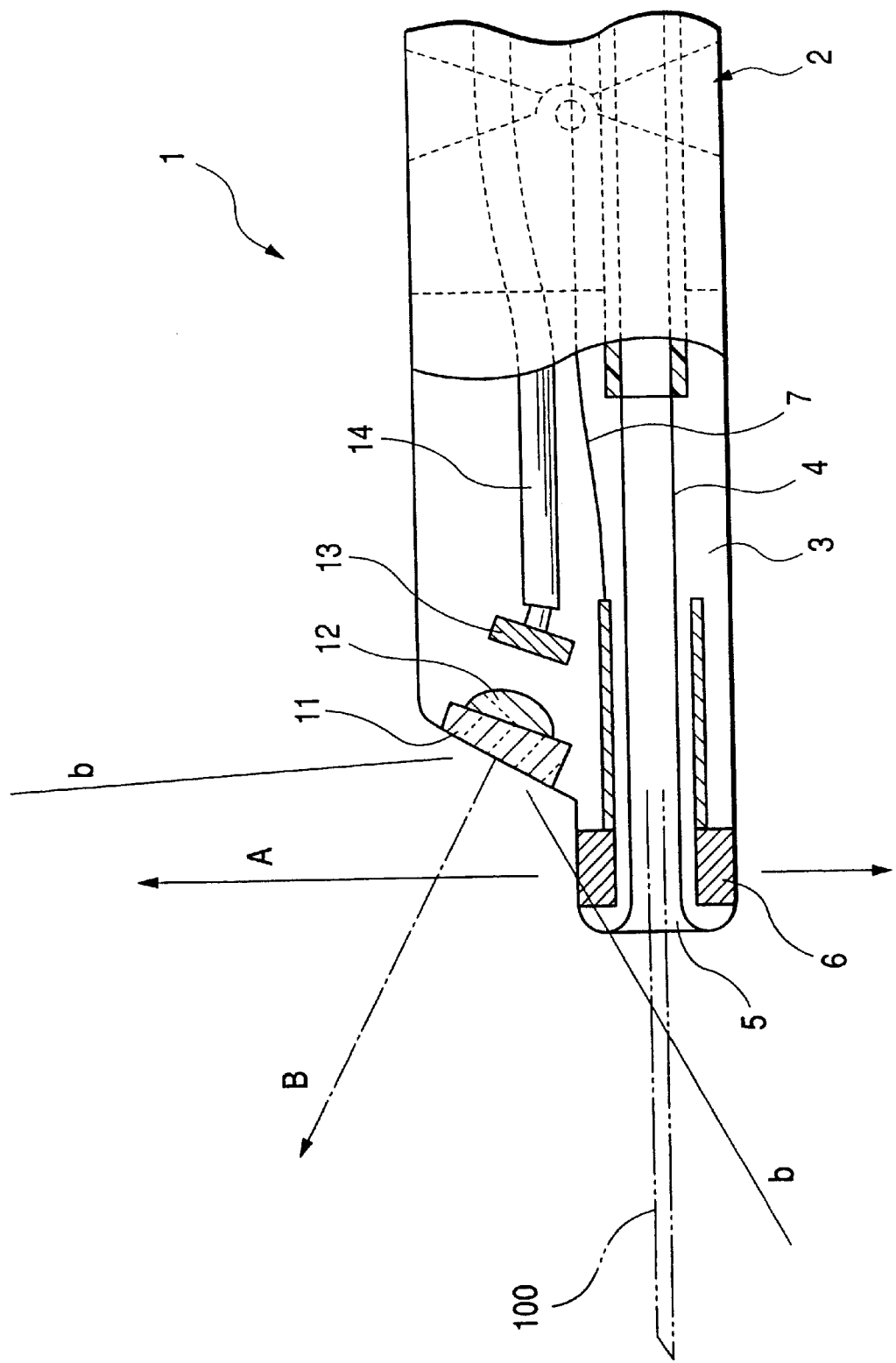
FIG. 1 shows diagrammatically a longitudinal section of the tip of an ultrasonic endoscope according to the first embodiment of the invention.

FIG. 1 shows an ultrasonic endoscope according to a first embodiment of the invention. The tip of the endoscope has an insertion portion 1, a curved portion 2 provided near its distal end to be capable of bending in any directions by remote control, and a tip housing 3 coupled to the distal end of the curved portion 2.

An instrument-inserting channel 4 into which an instrument 100 such as an injecting syringe is to be passed extends through the insertion portion 1 parallel to its longitudinal axis, with its exit opening 5 being provided forward at the distal end face of the tip housing 3. Hence, the distal end portion of an instrument 100 inserted into the channel 4 projects straight and forward from the tip housing 3.

Provided annularly around the exit opening 5 of the instrument-inserting channel 4 is an ultrasonic oscillator array 6 that is coaxial with the channel 4. The ultrasonic oscillator array 6 is made up of radially segmented ultrasonic oscillators arranged in a cylindrical form and they are adapted to transmit and receive ultrasonic waves alternatively to perform "radial" ultrasonic scan. The direction of scan is indicated by A. Reference numeral 7 represents a signal line for conveying the signals to transmit or receive the ultrasonic waves using the ultrasonic oscillator array 6.

The outside diameter of the ultrasonic oscillator array 6 is about one half the outside diameter of the tip housing 3 and in the distal end portion of the tip housing 3, only the ultrasonic oscillator array 6 projects forward of other parts of the insertion portion 1. That is, the outer diameter or the external size of the distal end portion of the tip housing 3 is reduced to the outer diameter of the external size of the ultrasonic oscillator array 6. An optical viewing window 11 is provided in an inclined surface that is formed slightly backward of the ultrasonic oscillator array 6.

An objective lens 12 is provided within the optical viewing window 11 and the imaging plane of a solid-state imaging device 13 coincides with the position in which the objective lens 12 forms the image of an object under examination. Indicated by 14 is a signal cable for transmitting the imaging signal and the like.

The viewing optical system used in this embodiment is intended for viewing forward at an angle. That is, a viewing optical axis B is directed obliquely forward with respect to the longitudinal axis of the insertion portion 1 to which the instrument-inserting channel 4 extends parallel. Note that due to the wide viewing angle of the optical system and on account of the provision of the optical viewing window 11 backward of the ultrasonic oscillator array 6, the instrument 100 projecting from the instrument-inserting channel 4 and the direction of ultrasonic scan with the ultrasonic oscillator array 6 are included within the viewing range (b—b). That is, both of the direction of the instrument-inserting channel 4 from which the instrument 100 projects, and the radial scan direction of the ultrasonic oscillator array 6 at least partially overlap with the viewing range or visual field (b—b) of the optical system made up of the objective lens 12 and the optical viewing window 11.

This not only enables the surface of the diseased part to be viewed optically at the same time as its cross-sectional image is being obtained by ultrasonic scan; the surgeon can also operate on the diseased part with the instrument 100 as it is manipulated under optical viewing.

Figure 2:
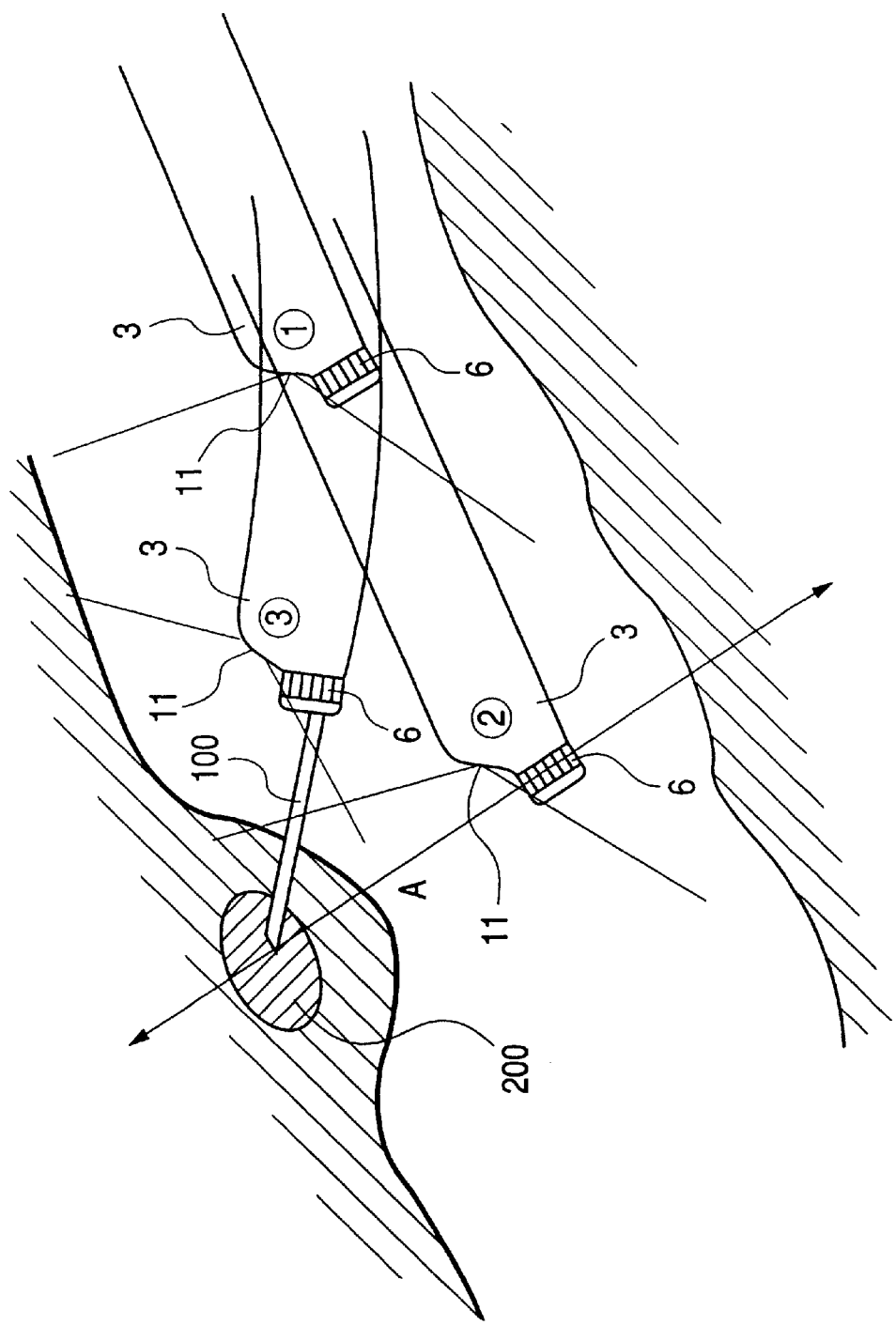
FIG. 2 shows diagrammatically how the ultrasonic endoscope is used in practice.

FIG. 2 shows how the ultrasonic endoscope having the structure described above is used in practice. If something abnormal such as a protuberance is found in a body cavity by optical viewing (①), the tip housing 3 is guided to the position of ultrasonic scan while the abnormality is visually confirmed under optical viewing (②). If a tumor 200 or the like is found within the protuberance by ultrasonic scan, an instrument 100 such as an injecting syringe is pierced into the tumor 200 under optical viewing (③) to apply the necessary treatment to the tumor 200 immediately.

Figure 3:
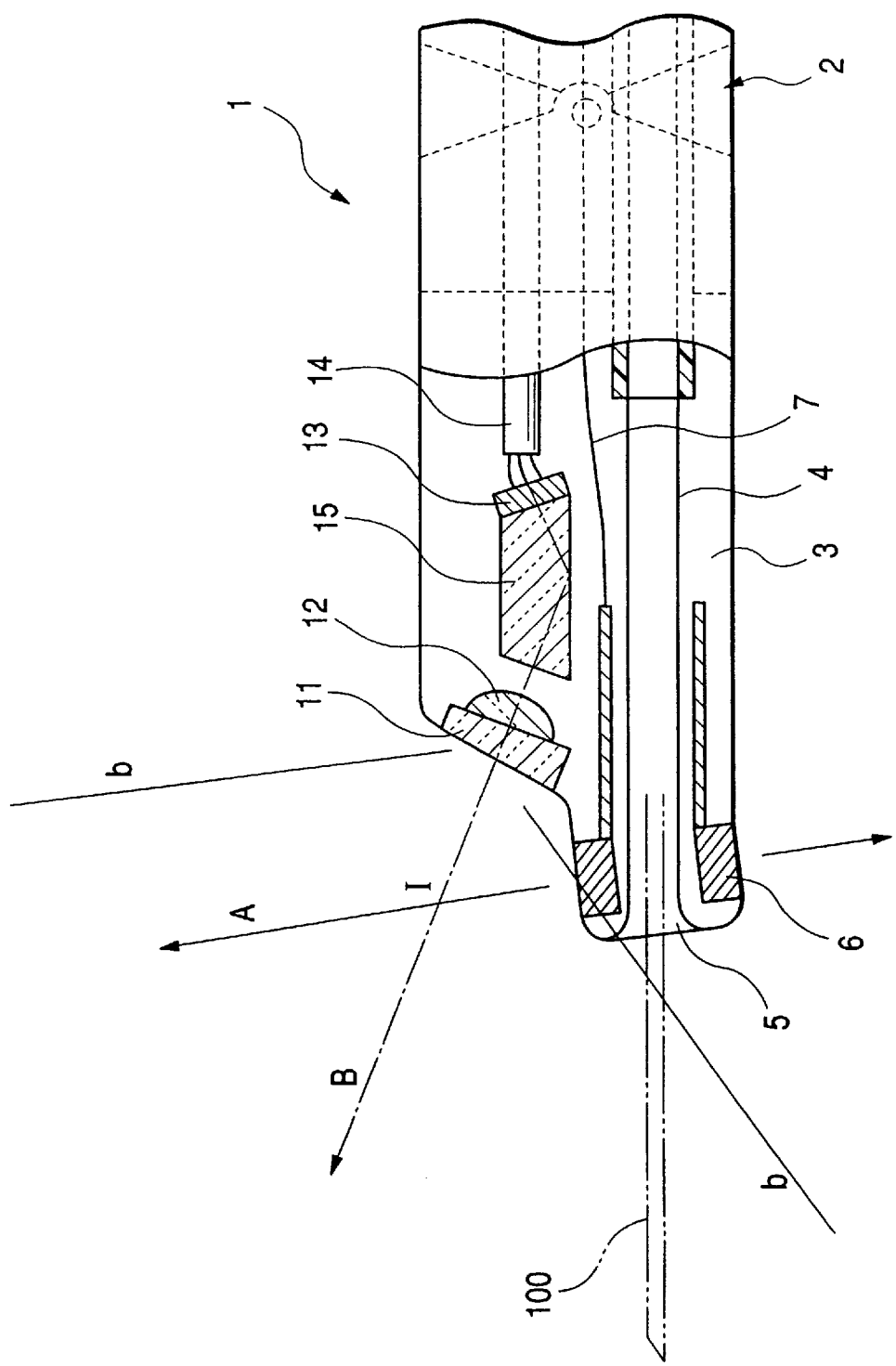
FIG. 3 shows diagrammatically a longitudinal section of the tip of an ultrasonic endoscope according to the second embodiment of the invention.

FIG. 3 shows an ultrasonic endoscope according to a second embodiment of the invention, in which the longitudinal axis of the annular ultrasonic oscillator array 6 is inclined with respect to that of the instrument-inserting channel 4 such that the ultrasonic scan direction A is away from the optical viewing window 11. That is, the ultrasonic oscillator array 6 is arranged obliquely so that the intersection I between the ultrasonic scan direction A of the ultrasonic oscillator array 6 and the viewing optical axis B of the optical system is located farther from the optical viewing window 11 in comparison to the first embodiment.

Given this structure, the ultrasonic scan direction A comes within the viewing range (b—b) more positively than in the first embodiment and this allows for easier optical viewing of an object located in the ultrasonic scan direction A. In the second embodiment, a prism 15 is additionally provided in the viewing optical system. For the other features of its structure, the second embodiment is identical to the first embodiment.

The invention is by no means limited to the embodiments described above and various modifications are possible as exemplified by transmitting an optically viewed image through an image guide fiber bundle.

In the invention, the instrument-inserting channel has its exit opening directed forward and formed at the distal end face of the insertion portion of an ultrasonic endoscope and an ultrasonic oscillator array is provided annularly around the exit opening of the channel; as a result, the distal end of the insertion portion is made sufficiently compact to reduce the pain the patient has to endure. Further, an optical viewing window for viewing forward at an angle that covers in its visual field both the distal end portion of an instrument projected from the instrument-inserting channel and the direction of ultrasonic scan with the ultrasonic oscillator array is provided backward of the array; as a result, the site under ultrasonic scan can be optically viewed at the same time, allowing reliable examination to be performed smoothly.

What is claimed is:

1. Tip of an ultrasonic endoscope comprising:
    an instrument-inserting channel formed with an exit opening directed forward and opened at a distal end face of an insertion portion of the endoscope;
    an ultrasonic oscillator array for radial scan that is provided annularly around the exit opening of the instrument-inserting channel; and
    an optical viewing window for viewing obliquely forward that is provided rearward of the ultrasonic oscillator array in such a way that its visual field covers both a distal end portion of an instrument projected from the instrument-inserting channel and a direction of ultrasonic scan with the ultrasonic oscillator array.

2. The tip of an ultrasonic endoscope according to claim 1, wherein the radial ultrasonic oscillator array is provided coaxially with the instrument-inserting channel.

3. The tip of an ultrasonic endoscope according to claim 1, wherein a longitudinal axis of the annular ultrasonic oscillator array is arranged obliquely with respect to a longitudinal axis of the instrument-inserting channel in such a direction that the direction of ultrasonic scan is away from said optical viewing window.

4. A tip of an ultrasonic endoscope, comprising:
    a tip housing having a first part defining a first external size, a second part adjacent to the first part and defining a second external size larger than the first external size and a slope connecting the first part to the second part;
    a annular ultrasonic oscillator array provided to the first part;
    an viewing optical system having an optical viewing window provided to the slope;
    an instrument-inserting channel passing through the tip housing and opened at an end face of the first part.

5. The tip of the ultrasonic endoscope according to claim 4, wherein the annular ultrasonic oscillator array is arranged around the instrument-inserting channel.

6. The tip of the ultrasonic endoscope according to claim 5, wherein the annular ultrasonic oscillator array is coaxially arranged with respect to the instrument-inserting channel.

7. The tip of the ultrasonic endoscope according to claim 5, wherein an axis about which the annular ultrasonic oscillator array is arranged is inclined with respect to a longitudinal axis of the instrument-inserting channel.

8. The tip of the ultrasonic oscillator according to claim 5, wherein the annular ultrasonic oscillator array is coaxially arranged with respect to the first part.

9. The tip of the ultrasonic endoscope according to claim 8, wherein the annular ultrasonic oscillator array is coaxially arranged with respect to the instrument-inserting channel.

10. The tip of the ultrasonic endoscope according to claim 8, wherein an axis about which the annular ultrasonic oscillator array is arranged is inclined with respect to a longitudinal axis of the instrument-inserting channel.

11. The tip of the ultrasonic endoscope according to claim 4, wherein the viewing optical system defines a viewing optical axis that is inclined with respect to a longitudinal axis o the instrument-inserting channel.

12. The tip of the ultrasonic endoscope according to claim 11, wherein the viewing optical axis intersects a radial scan direction of the annular ultrasonic oscillator.

13. The tip of the ultrasonic endoscope according to claim 4, wherein both of a longitudinal axis of the instrument-inserting channel and a radial scan direction of the annular ultrasonic oscillator at least partially overlap with a viewing range of the viewing optical system.

14. The tip of the ultrasonic endoscope according to claim 4, wherein both of the annular ultrasonic oscillator and the end face of the first part are at least partially located within a space bounded by a viewing range of the viewing optical system.

* * * * *